US012799066B2

(12) United States Patent
Jordan et al.

(10) Patent No.: US 12,799,066 B2
(45) Date of Patent: Nov. 17, 2026

(54) METHOD FOR PREPARING 3-HYDROXYPROPIONATE ESTERS

(71) Applicant: Novomer LLC, Bainbridge, GA (US)

(72) Inventors: Abraham J. Jordan, Rochester, NY (US); Christopher A. DeRosa, Rochester, NY (US)

(73) Assignee: Novomer LLC, Bainbridge, GA (US)

( * ) Notice: Subject to any disclaimer, the term of this patent is extended or adjusted under 35 U.S.C. 154(b) by 390 days.

(21) Appl. No.: 18/411,499

(22) Filed: Jan. 12, 2024

(65) Prior Publication Data

US 2025/0230120 A1 Jul. 17, 2025

(51) Int. Cl.
*C07C 67/03* (2006.01)

(52) U.S. Cl.
CPC .................................... *C07C 67/03* (2013.01)

(58) Field of Classification Search
CPC ...................................................... C07C 67/03
See application file for complete search history.

(56) References Cited

U.S. PATENT DOCUMENTS

| | | | | |
|---|---|---|---|---|
| 6,852,865 | B2 | 2/2005 | Coates et al. | |
| 8,445,703 | B2 * | 5/2013 | Allen | C07D 305/12 549/328 |
| 8,481,756 | B1 | 7/2013 | Coates et al. | |
| 9,850,192 | B2 | 12/2017 | Harris et al. | |
| 11,046,642 | B2 | 6/2021 | Karp et al. | |
| 2018/0327345 | A1 | 11/2018 | Pazicky et al. | |
| 2022/0049051 | A1 * | 2/2022 | Machat | C08G 63/823 |

FOREIGN PATENT DOCUMENTS

| | | | |
|---|---|---|---|
| WO | 2022216491 | A1 | 10/2022 |
| WO | 2022221086 | A1 | 10/2022 |
| WO | 2022221266 | A1 | 10/2022 |
| WO | 2023283594 | A1 | 1/2023 |

OTHER PUBLICATIONS

Gresham, T.L. et al., ?-Propiolactone. V. Reaction with Alcohols—J. Am. Chem. Soc 1948, 70, 3, 1004-1006—direct conversion from bPL to esters of 3-HP (3 pages).

* cited by examiner

*Primary Examiner* — Sikarl A Witherspoon
(74) *Attorney, Agent, or Firm* — Young Basile Hanlon & MacFarlane, P.C.

(57) ABSTRACT

A method includes contacting an epoxide and carbon monoxide to form a beta-propiolactone compound; contacting the beta-propiolactone compound and an initiator to form poly-3-hydroxy-propionate; and contacting the poly-3-hydroxy-propionate, an alcohol, and an esterification catalyst at a temperature sufficient to form an ester compound terminated by a hydroxyl group. The ester compound may be free of carbonylation and/or esterification catalysts.

20 Claims, 3 Drawing Sheets

METHOD FOR PREPARING 3-HYDROXYPROPIONATE ESTERS

TECHNICAL FIELD

This disclosure relates to a method of preparing 3-hydroxypropionate esters from poly-3-hydroxypropionate.

BACKGROUND

Esters may be used in perfumes, essential oils, and fabrics. Alternatively, esters may be converted to other organic compounds such as nitriles useful in hard plastics. Esters may be formed from acids containing oxygen. For example, a common formation reaction is a substitution reaction between a carboxylic acid and an alcohol. Alternatively, esters may also be formed from polymers. Currently, esters formed from polymers utilize many steps to remove unwanted contaminants.

Accordingly, what is needed is a method for producing esters from polymers that minimize steps to yield desirable ester compositions.

SUMMARY

Disclosed herein is a method including contacting an epoxide and carbon monoxide to form a beta-propiolactone compound; contacting the beta-propiolactone compound and an initiator to form poly-3-hydroxy-propionate; and contacting the poly-3-hydroxy-propionate, an alcohol, and an esterification catalyst at a temperature sufficient to form an ester compound terminated by a hydroxyl group.

Disclosed herein is a composition of an ester compound that is a residue of a poly-3-hydroxy-propionate, a residue of a poly-3-hydroxy-propionate initiator, and a residue of an esterification catalyst.

The epoxide may have a formula according to formula I:

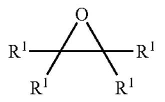

where each $R^1$ is independently selected from one or more of hydrogen, straight or branched alkyl groups, aryl groups, alkyl-aryl groups, aryl-alkyl groups, or any combination thereof.

The beta-propiolactone compound may have a formula according to the following formula II below:

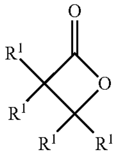

where each $R^1$ may be independently selected from one or more of hydrogen, straight or branched alkyl groups, aryl groups, alkyl-aryl groups, aryl-alkyl groups, or any combination thereof.

The ester compound may have a hydroxyl group connected to an alkyl chain of at least three carbons and have the following formula III below

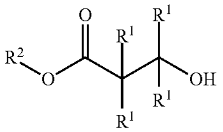

where each $R^1$ may be independently selected from one or more of hydrogen, straight or branched alkyl groups, aryl groups, alkyl-aryl groups, aryl-alkyl groups, or any combination thereof, and in which $R^2$ may be a residue of the alcohol having one of a straight or branched alkyl group, aryl group, alkyl-aryl group, aryl-alkyl group, or any combination thereof. The ester compound of the composition may include any one of the following formulas:

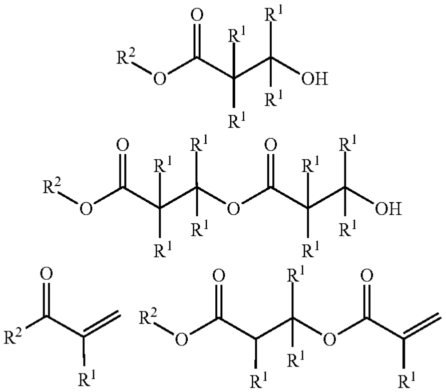

in which each $R^1$ may be independently selected from one or more of hydrogen, straight or branched alkyl groups, aryl groups, alkyl-aryl groups, aryl-alkyl groups, or any combination thereof, and in which each $R^2$ may be a residue of the alcohol independently having one of a straight or branched alkyl group, aryl group, alkyl-aryl group, aryl-alkyl group, or any combination thereof.

The epoxide and the carbon monoxide may be contacted in a first chamber in the presence of a carbonylation catalyst. The method may include separating the beta-propiolactone compound from the carbonylation catalyst so that the beta-propiolactone compound is free of residues of the carbonylation catalyst. The beta-propiolactone compound and the initiator may be contacted in a second chamber that is separated from the first chamber. The poly-3-hydroxy-propionate, the alcohol, and the esterification catalyst may be contacted in the second chamber or a third chamber that are each separated from the first chamber. The contacting of the poly-3-hydroxy-propionate by the alcohol and the esterification catalyst may be free of polymerization inhibitors. The poly-3-hydroxy-propionate may be heated to a reaction temperature greater than a melting temperature of poly-3-hydroxy-propionate. The reaction temperature may be greater than or equal to 78° C. and less than or equal to 180° C. The contacting of the poly-3-hydroxy-propionate, the alcohol, and the esterification catalyst may be conducted at a temperature greater than or equal to 100° C. and less than or equal to 180° C. The method may include applying less than or equal to 5 atm of pressure to increase the boiling point of the alcohol so that the reaction is performed in the liquid phase. The ester compound may be separated from the alcohol and/or the esterification catalyst by distillation, filtration, or oxidation. The ester compound may be free of the beta-propiolactone compound, the initiator, the carbon monoxide, or the epoxide. The ester compound may be nitrated to form acrylonitrile. The esterification catalyst may facilitate formation of the ester compound. The esterification catalyst may be an acid catalyst including one or more of the following: sulfuric acid, phosphoric acid, p-toluenesulfonic acid, camphorsulfonic acid, Amberlite IR 200 hydrogen form, and diphenyl phosphate. The esterification catalyst may be a sulfur catalyst. The alcohol may have one or more straight or branched alkyl, aryl, alkyl-aryl, or aryl-alkyl groups. The one or more straight or branched alkyl groups may include one or more methyl, ethyl, propyl, or butyl groups. The straight alkyl group may include methanol, ethanol, propanol, or butanol. The branched alkyl group may include isopropanol, isobutanol, sec-butanol, or tert-butanol. The one or more aryl groups may include one or more of phenyl, tolyl, xylyl, or naphthyl.

The residue of the poly-3-hydroxy-propionate initiator may be present in a mass percent of about 0.01 to about 5. The residue of the catalyst may be present in a weight percent [or ppm] of about 0.1 to about 20.

The present techniques provide for a pathway to yield ester compounds terminated by a hydroxyl group with little or no undesirable side products by forming polypropiolactones via a two step synthesis of carbonylation and subsequent polymerization. Because of this, ester compounds or derivatives thereof are attained that are free of carbonylation catalysts and free of undesirable purities that may impact downstream chemical synthesis, such as for production of acrylonitriles.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1:
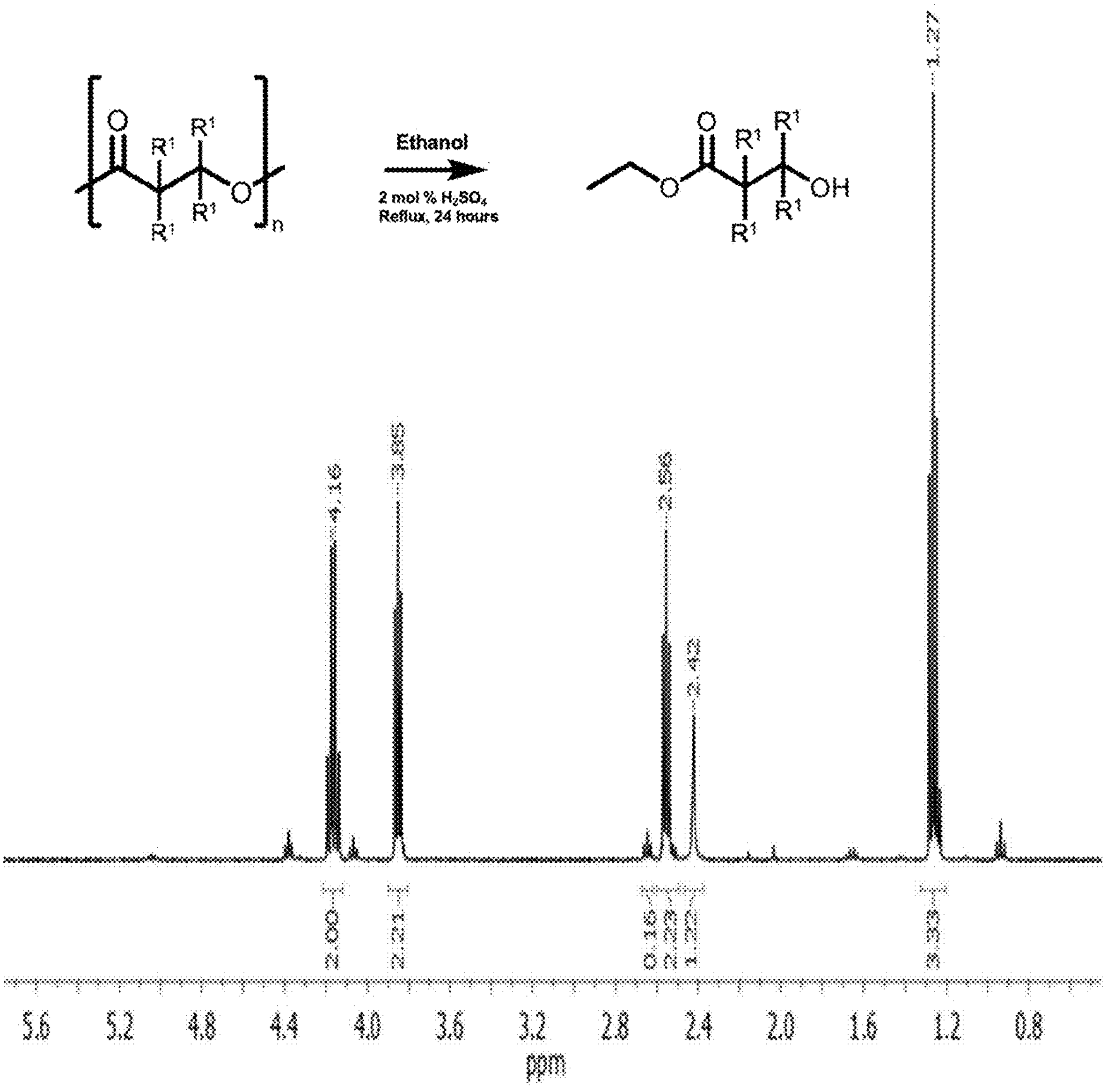
FIG. 1 illustrates a reaction scheme of contacting a polypropiolactone polymer, ethanol, and a catalyst to form a an ester compound and associated NMR data of ester compounds formed from the disclosed scheme.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

One or more as used herein means that at least one, or more than one, of the recited components may be used as disclosed. Residue with respect to an ingredient or reactant used to prepare the polymers or structures disclosed herein means that portion of the ingredient that remains in the polymers or structures after inclusion as a result of the methods disclosed herein. Substantially or essentially all of as used herein means that greater than 90 percent of the referenced parameter, composition, structure, or compound meet the defined criteria, greater than 95 percent, greater than 99 percent of the referenced parameter, composition or compound meet the defined criteria, or greater than 99.5 percent of the referenced parameter, composition or compound meet the defined criteria. Substantially or essentially free as used herein means that the reference parameter, composition, structure, or compound contains about 10 percent or less, about 5 percent or less, about 1 percent or less, about 0.5 percent or less, about 0.1 percent or less, or about 0.01 percent or less. Portion as used herein means less than the full amount or quantity of the component in the composition, stream, or both. Precipitate as used herein means a solid compound in a slurry or blend of liquid and solid compounds. The ingredients or products may exist in different states during the processes disclosed, such as solid, liquid, or gaseous state. Phase refers to a portion of a reaction mixture that is not soluble in another part of the reaction mixture. Parts per weight means parts of a component relative to the total weight of the overall composition. Composition or mixture as used herein includes all components in a stream, reactant stream, product stream, slurry, precipitate, solution, liquid, solid, gas, or any combination thereof that are containable within a single vessel. In other words, the mixture may include components that are solid, gaseous (i.e., volatile), and/or liquid when at room temperature (i.e., 25 degrees Celsius) or when exposed to elevated temperatures. Certain polymers disclosed can comprise one or more asymmetric centers, and thus can exist in various stereoisomeric forms, e.g., enantiomers and/or diastereomers. The polymers and compositions thereof may be in the form of an individual enantiomer, diastereomer or geometric isomer, or may be in the form of a mixture of stereoisomers. The polymers disclosed may be enantiopure compounds. Disclosed are mixtures of enantiomers or diastereomers. In certain structures disclosed in this application parts of the structure are connected by a dotted line - - - - which indicates that the connected structures are ionically bonded together.

As described herein, compounds disclosed may contain "optionally substituted" moieties. The term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned are those that result in the formation of stable or chemically feasible compounds. The term The term "beta lactone", as used herein, refers to a substituted or unsubstituted cyclic ester having a four-membered ring comprising an oxygen atom, a carbonyl group and two optionally substituted methylene groups. When unsubstituted, the beta lactone is referred to as propiolactone. Substituted beta lactones include monosubstituted, disubstituted, trisubstituted, and tetrasubstituted beta lactones. Such beta lactones may be further optionally substituted as defined herein. The beta lactones comprise a single lactone moiety. The beta lactones may comprise two or more four-membered cyclic ester moieties. The beta-lactones described herein may correspond to the following formula II below:

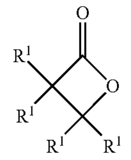

where each $R^1$ may be independently selected from the group consisting of hydrogen; straight or branched alkyl groups; halogenated alkyl chains; phenyl groups; optionally substituted aromatic alkyl groups; aryl groups; aryl-alkyl groups; alkyl-aryl groups; optionally substituted phenyl; optionally substituted alkyl groups, or any combination thereof.

The term "epoxide", as used herein, refers to a substituted or unsubstituted oxirane. Such substituted oxiranes include monosubstituted oxiranes, disubstituted oxiranes, trisubstituted oxiranes, and tetrasubstituted oxiranes. Such epoxides may be further optionally substituted as defined herein. The epoxides may comprise a single oxirane moiety. The epoxides comprise two or more oxirane moieties. The epoxides described herein may correspond to the following formula I below:

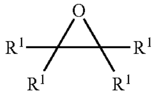

where $R^1$ is described herein.

The term "polymer", as used herein, refers to a molecule of high relative molecular mass, the structure of which comprises the multiple repetition of units derived, actually or conceptually, from molecules of low relative molecular mass. The polymer may be comprised of beta lactone monomers (e.g., polypropiolactone) or derived therefrom. Such polymers are also referred to as poly(3-hydroxypropionate). The polymers disclosed may be a copolymer, terpolymer, heteropolymer, block copolymer, or tapered heteropolymer incorporating two or more different monomers.

Disclosed is a method which includes contacting an epoxide and carbon monoxide to form a beta-propiolactone compound, contacting the beta-propiolactone compound and an initiator to form poly-3-hydroxy-propionate, and contacting the poly-3-hydroxy-propionate, an alcohol, and an esterification catalyst at a temperature sufficient to form an ester compound terminated by a hydroxyl group. The step of contacting the epoxide and the carbon monoxide yields the beta-propiolactone compound that is free of carbonylation catalyst because the beta-propiolactone compound is separated from the carbonylation catalyst during formation, for example, by gas-liquid separation techniques. In this state, the beta-propiolactone compound is useful in the formation of polymers, such as poly-3 hydroxy-propionate, by initiators to achieve the polymers with high levels of purity and desirable properties. These polymers can be transported and/or contacted with esterification catalysts, without further purification or isolation, and alcohols to yield esters that that are essentially free of undesirable impurities, such as residues of carbonylation catalysts. This is beneficial because the present techniques avoid costly purification steps in downstream processes that use esters to make other compounds and the formed ester compounds can be immediately transported and/or used in downstream processes.

Figure 3:
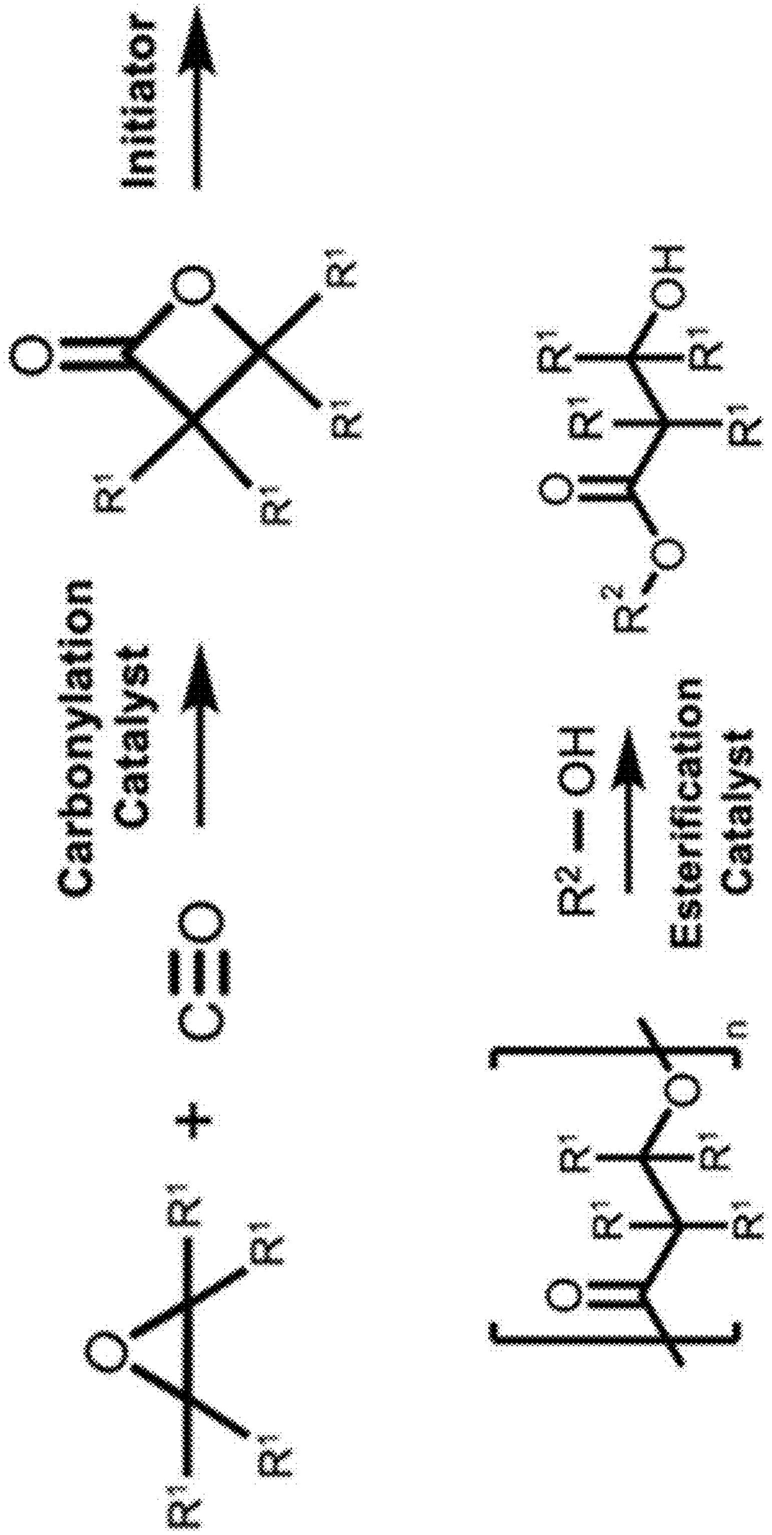
FIG. 3 illustrates a reaction scheme to form one or more ester compounds.

The method may proceed as shown in FIG. 3:

in which each $R^1$, $R^2$, and n are defined herein.

The epoxide and the carbon monoxide may be contacted under conditions sufficient to form the beta-propiolactone compound.

Examples of the process conditions and solvents for formation of the beta-propiolactone compound can be found in at least U.S. Pat. No. 8,445,703, which are incorporated herein by reference. The epoxide and the carbon monoxide may be contacted in the presence of the carbonylation catalyst. The carbonylation catalyst may have any structure that includes a sufficient cationic Lewis acid having a metal center and metal carbonyl anion ionically bound to the Lewis acid. The carbonylation catalyst may be any compound that has carbonylative catalytic activity with an epoxide and/or lactone (e.g., acetolactone, a propiolactone, a butyrolactone, a valerolactone, caprolactone, or any combination thereof).

The Lewis acid functions to provide the cationic component of the carbonylation catalyst. The Lewis acid may be a metal centered compound, a metal complex, or both that is configured to be anionically balanced by one or more metal carbonyls. The Lewis acid component of the carbonylation catalyst may include a dianionic tetradentate ligand. The Lewis acid may include one or more porphyrin derivatives, salen derivatives, dibenzotetramethyltetraaza[14]annulene (tmtaa) derivatives, phthalocyaninate derivatives, derivatives of the Trost ligand, tetraphenylporphyrin derivatives, tetramethyl-tetra-aza-annulene type, and corrole derivatives. In some examples, where the carbonylation catalysts used in the disclosed methods include a cationic Lewis acid including a metal complex, the metal complex has the formula $[(L^c)_v M_b]^{z+}$, where:

L is a ligand where, when two or more L are present, each may be the same or different;

M is a metal atom where, when two M are present, each may be the same or different;

v is an integer from 1 to 4 inclusive;

b is an integer from 1 to 2 inclusive; and z is an integer greater than 0 that represents the cationic charge on the metal complex.

In other examples, the Lewis acid or metal centered compound may have a structure of metal complex I or II. Where the Lewis acid has the metal complex I, the metal complex may be the following configuration:

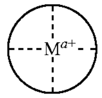

Metal Complex (I):

where

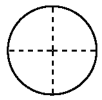

is a multidentate ligand;

M is a metal atom coordinated to the multidentate ligand; and a is the charge of the metal atom and ranges from 0 to 2. In some examples, the metal complexes include structures according to metal complex II.

In other examples, the Lewis acid may have the metal complex having the formula of metal complex II:

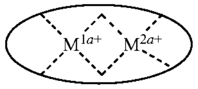

Metal Complex (II):

Where a is as defined above and each a may be the same or different,

M1 is a first metal atom;

M2 is a second metal atom; and

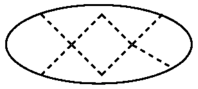

comprises a multidentate ligand system capable of coordinating both metal atoms.

As stated above, the Lewis acid may include or be one or more of porphyrin derivatives (ligand structure 1), salen derivatives (ligand structure 2), dibenzotetramethyltetraaza [14]annulene (tmtaa) derivatives (ligand structure 3), phthalocyaninate derivatives (ligand structure 4), derivatives of the Trost ligand (ligand structure 5), tetraphenylporphyrin derivatives (ligand structure 6), and corrole derivatives (ligand structure 7). The configurations of each of the ligand structures is shown and described below:

Ligand Structures 1-7

1

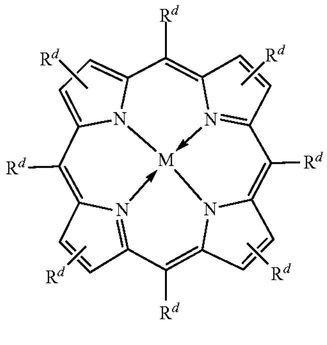

2

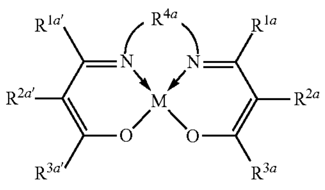

-continued

3

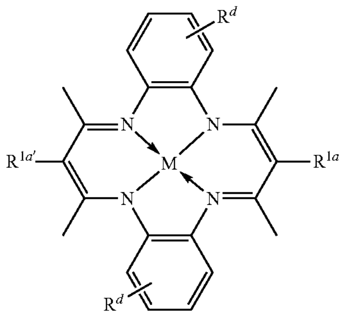

4

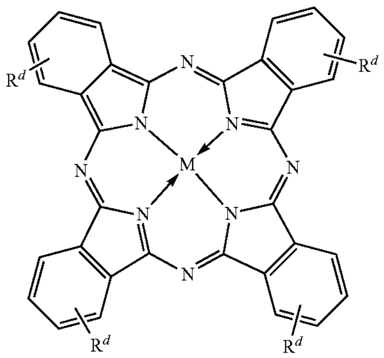

5

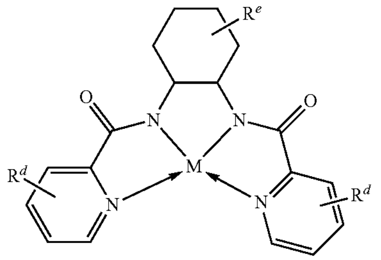

6

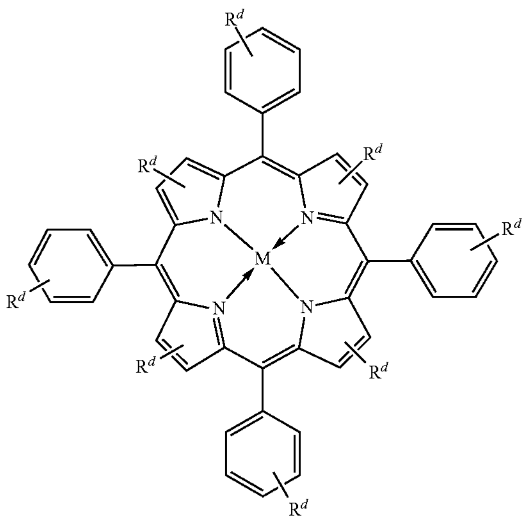

-continued

7

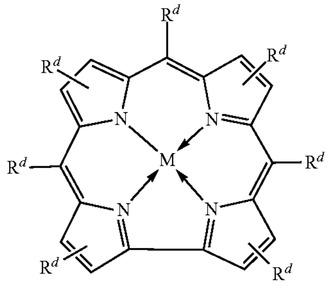

where M is a metal;

where each ligand structure has an ionic charge of 0 to +4;

where $R^{1a}$, $R^{1a'}$, $R^{2a}$, $R^{2a'}$, $R^{3a}$, $R^{3a'}$, $R^d$, and $R^e$ at each occurrence is independently hydrogen, halogen, —OR4, —$NR^y_2$, —SR, —CN, —$NO_2$, —$SO_2R^y$, —SORY, —$SO_2NR^y_2$; —CNO, —$NRSO_2R^y$, —NCO, —$N_3$, —$SiR_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6 to 10 membered aryl; 5 to 10 membered heteroaryl having 1-4 heteroatoms independently selected from nitrogen, oxygen, and sulfur; and 4 to 7 membered heterocyclic having 1-2 heteroatoms independently selected from the group consisting of nitrogen, oxygen, and sulfur, where two or more $R^d$ groups may be taken together to form one or more optionally substituted rings;

where each $R^y$ is independently hydrogen, an optionally substituted group selected the group consisting of acyl; carbamoyl, arylalkyl; 6 to 10 membered aryl; $C_{1-12}$ aliphatic; $C_{1-12}$ heteroaliphatic having 1-2 heteroatoms independently selected from the group consisting of nitrogen, oxygen, and sulfur; 5 to 10 membered heteroaryl having 1-4 heteroatoms independently selected from the group consisting of nitrogen, oxygen, and sulfur; 4 to 7 membered heterocyclic having 1-2 heteroatoms independently selected from the group consisting of nitrogen, oxygen, and sulfur; an oxygen protecting group; and a nitrogen protecting group; two $R^y$ on the same nitrogen atom are taken with the nitrogen atom to form an optionally substituted 4 to 7 membered heterocyclic ring having 0-2 additional heteroatoms independently selected from the group consisting of nitrogen, oxygen, and sulfur;

wherein any of ($R^{2a'}$ and $R^{3a}$), ($R^{2a}$ and $R^{3a}$), ($R^a$ and $R^{2a}$), and ($R^{1a'}$ and $R^{2a'}$) may optionally be taken together with the carbon atoms to which they are attached to form one or more rings which may in turn be substituted with one or more R groups;

where each $R^4$ independently is a hydroxyl protecting group or $R^y$; and $R^{4a}$ is selected from the group consisting of:

e)

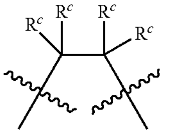

-continued f)

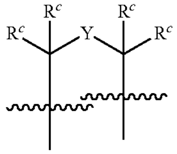

g)

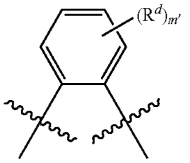

h)

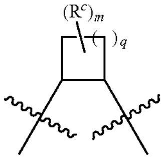

where $R^c$ is described above and two or more $R^c$ groups may be taken together with the carbon atoms to which they are attached and any intervening atoms to form one or more rings; when two $R^c$ groups are attached to the same carbon atom, they may be taken together along with the carbon atom to which they are attached to form a moiety selected from the group consisting of: a 3- to 8-membered spirocyclic ring, a carbonyl, an oxime, a hydrazone, an imine; and an optionally substituted alkene;

Y is a divalent linker selected from the group consisting of: —$NR^y$—, —N(R)C(O)—, —C(O)$NR^y$-, —O—, —C(O)—, —OC(O)—, —C(O)O—, —S—, —SO—, —$SO_2$—, —C(═S)—, —C(═$NR^y$)—, —N═N—; a polyether; a $C_3$ to Cg substituted or unsubstituted carbocycle; and a $C_{1-8}$ substituted or unsubstituted heterocycle; m' is 0 or an integer from 1 to 4;

q is 0 or an integer from 1 to 4, inclusive; and x is 0, 1, or 2.

In metal complexes 1-2 and/or ligand structures 1-7, M1 and M2 may each independently be a metal atom selected from the periodic table groups 2-13, inclusive. M, M1, M2, or a combination thereof may be a transition metal selected from the periodic table groups 4, 6, 11, 12 and 13. M, M1, M2, or a combination thereof may be aluminum, chromium, titanium, indium, gallium, zinc, cobalt, copper, or any combination thereof. M1 and M2 may be the same or different metals. M1 and M2 may be the same metal but have different oxidation states. M, M1, M2, or a combination thereof may have an oxidation state of +2. M1 or M2 may be Zn(II), Cu(II), Mn(II), Co(II), Ru(II), Fe(II), Co(II), Rh(II), Ni(II), Pd(II) or Mg(II). M1 may be Cu(II). M, M1, M2, or a combination thereof may be Zn(II), Cu(II), Mn(II), Co(II), Ru(II), Fe(II), Co(II), Rh(II), Ni(II), Pd(II) or Mg(II). M, M1, M2, or a combination thereof may have an oxidation state of +3. M, M1, M2, or a combination thereof may be Al(III), Cr(III), Fe(III), Co(III), Ti(III) In(III), Ga(III) or Mn(III). M, M1, M2, or a combination thereof may have an oxidation state of +4. M, M1, M2, or a combination thereof may be Ti(IV) or Cr(IV).

In some Lewis acids, one or more polar ligands may coordinate to M, M1, M2, or a combination thereof and fill the coordination valence of the metal atom. The Lewis acid may include any number of polar ligands to fill the coordination valence of the metal atom. For example, the Lewis acid may include one or more polar ligands, two or more polar ligands, three or more polar ligands, four or more polar ligands, or a plurality of polar ligands. The polar ligand may be a solvent. The polar ligand may be any compound with at least two free valence electrons. The polar ligand may be aprotic. The compound may be tetrahydrofuran, diethyl ether, acetonitrile, carbon disulfide, pyridine, epoxide, ester, lactone, or a combination thereof.

The metal carbonyl of the carbonylation catalyst functions to provide the anionic component of the carbonylation catalyst. The carbonylation catalyst may include one or more, two more, or a mixture of metal carbonyls. The metal carbonyl may be capable of ring-opening an epoxide and facilitating the insertion of CO into the resulting metal carbon bond. In some examples, the metal carbonyl may include an anionic metal carbonyl moiety. In other examples, the metal carbonyl compound may include a neutral metal carbonyl compound. The metal carbonyl may include a metal carbonyl hydride or a hydrido metal carbonyl compound. The metal carbonyl may be a pre-catalyst which reacts in situ with one or more reaction components to provide an active species different from the compound initially provided. The metal carbonyl includes an anionic metal carbonyl species in some examples, the metal carbonyl may have the general formula $[Q_dM'_e(CO)_w]^{y+}$, where Q is an optional ligand, M' is a metal atom, d is an integer between 0 and 8 inclusive, e is an integer between 1 and 6 inclusive, w is a number such as to provide the stable anionic metal carbonyl complex, and y is the charge of the anionic metal carbonyl species. The metal carbonyl may include monoanionic carbonyl complexes of metals from groups 5, 7 or 9 of the periodic table or dianionic carbonyl complexes of metals from groups 4 or 8 of the periodic table. The metal carbonyl may contain cobalt, manganese, ruthenium, or rhodium. Exemplary metal carbonyls may include $[Co(CO)_4]$—, $[Ti(CO)e]^{2}$-, $[V(CO)_6]$—, $[Rh(CO)_4]$—, $[Fe(CO)_4]^{2}$—, $[Ru(CO)_4]^{2}$—, $[Os(CO)_4]^{2}$, $[Cr_2(CO)io]^{2-}$, $[Fe_2(CO)_8]^{2}$—, $[Tc(CO)_5]^{-}$, $[Re(CO)_5]^{-}$; and $[Mn(CO)_5]^{-}$. The metal carbonyl may be a mixture of two or more anionic metal carbonyl complexes in the carbonylation catalysts used in the methods.

Additional desirable carbonylation catalysts and techniques to make these catalysts may be found in publication U.S. Pat. No. 6,852,865B2 and U.S. Pat. No. 8,481,756B1 and WO2023283594A1 and WO2022216491A1 all of which are incorporated herein in their entirety.

The epoxide and the carbon monoxide may be contacted in the presence of a carbonylation catalyst under any conditions sufficient to form beta propopiolactone. The epoxide carbon monoxide (i.e., reactants) and catalyst may be contacted with any molar or equivalent ratio sufficient to form the desired beta propiolactone with low amounts of side products. Typically, the concentration of catalyst as given by the molar or equivalent ratio of liquid reactant/catalyst (liquid reactant being the epoxide, lactone or combination thereof as described). Desirably, the reactant is the epoxide and the reactant/catalyst molar ratio is the epoxide/catalyst ratio. The ratio is understood to mean the reactant/catalyst ratio of the epoxide and/or lactone and catalyst introduced into the reaction vessel. Generally, the reactant/catalyst ratio is at least 1500 or greater and may be 1750, 2000 2200, 2500 or 2800 to about 50,000, 25,000 or 20,000. The epoxide and carbon monoxide may be contacted under a temperature sufficient to form beta propiolactone and to avoid undesirable side reactions from under or overheating the reactants. The temperature may be about 85 degrees C. or more, about 95 degrees C. or more, or about 105 degrees C. or more. The temperature may be about 130 degrees C. or less, about 120 degrees C. or less, or about 110 degrees C. or less. The epoxide and the carbon monoxide may be contacted under pressure sufficient to form beta propiolactone is formed. Pressure may be adjusted to form the beta propiolactone in a form that is more easily separated from the reactants. Pressure may be maintained to mitigate undesirable side reactions. The pressure may be at least 700 psi or more, 900 psi or more, 11000 psi or more. The pressure may be 3000 psi or less, about 2000 psi or less or about 1500 psi or less.

The epoxide and the carbon monoxide may be contacted in the presence of the carbonylation catalyst in a first chamber. The first chamber may be configured to receive the epoxide, the carbon monoxide, and the carbonylation catalyst. The epoxide may be fed into the first chamber as a gas. The epoxide may fed into the first chamber as a liquid. The carbon monoxide can be provided either as a pure stream or as a mixture of the carbon monoxide and one or more additional gases. Additional gases may be one or more gases found in a syngas stream, such as hydrogen gas, carbon dioxide, or methane or a combination of any thereof. The contacting may form the beta-propiolactone compound in the form of a product stream that is free of the reactants or is a pure form (i.e., containing about 5 weight percent or less, about 1 weight percent or less, or 0.1 with percent or less of impurities or reactants based on the total weight of the product stream) of beta propiolactone.

The beta-propiolactone compound product stream may be purified by separating the carbonylation catalyst from the product stream so that the beta-propiolactone compound is free of residues from the carbonylation catalyst. Additionally, the beta-propiolactione may be produced at a pressure or temperature such that the beta-propiolactone is a gaseous form that is separated from the carbonylation catalyst is one or more product streams. Such separation may be integrated so that substantially all carbonylation catalyst is removed from the beta-propiolactone product stream prior to feeding the stream into a second chamber. The first chamber may be equipped with multiple outlets to remove beta propiolactone, excess epoxide and/or carbon monoxide, carbonylation catalysts, solvents, or any combination thereof such that beta propiolactone is yielded in a substantially pure form. Additional techniques to form beta propiolactones can be found in publication WO2022221086A1 which is incorporated herein by reference.

The separation of the carbonylation catalyst may be performed by any technique sufficient to separate liquid-liquid, liquid-solid, or liquid-gas mixtures. The carbonylation catalyst or other solid components may be removed by nanofiltration on a nanofiltration membrane. The nanofiltration membrane may be an organic solvent-stable nanofiltration membrane. The nanofiltration membrane may further be used in combination with an organic solvent or organic solvent system compatible with the carbonylation reaction and the nanofiltration membrane. The nanofiltration membrane may be selected in combination with the organic solvent or solvents such that the process achieves predetermined levels of lactone formation and catalyst separation. Additional separation techniques known to the skilled artisan may be utilized to remove one or more of the reactants or solvents used in the carbonylation process from the beta propiolactone product stream.

The beta-propiolactone compound product stream may be fed into the second chamber. The second chamber may be separated from the first chamber so that the second chamber is substantially free of all carbonylation catalyst residues.

Carbonylation catalyst residues may include one or more metal carbonyls, lewis acids, metals, ligands, or any combination thereof. The beta-propiolactone compound product stream may be contacted by the initiators described herein in the second chamber to form a polymer. The initiator may be fed from an initiator source into the second chamber. The initiator may initiate polymerization of the beta-propiolactone compound to form the one or more polymers described herein. The initiator may ring open the beta-propiolactone polymer to form intermediates that form repeating units derived from ring opened beta-propiolactones. The polymer may have a structure according to formula III. The polymer formed may be poly-3-hydroxy-propionate. The initiator may include one or more of alcohols, quaternary ammonium salts, carboxylate salts, phosphates, carboxylic acids, amines, halides, sulfonic acids, or any combination thereof.

The formed polymer may be prepared from a ratio of the beta-propiolactone compound to the initiators selected to prepare a polymer of the desired molecular weight. The ratio of beta propiolactone compound to initiator may selected to have acceptable amounts of initiator residues in downstream ester compounds formed from the claimed methods. For example, the mole ratio may be 10:1 or greater, 100:1 or greater, 1,000:1, or greater, 2,000:1 or greater, 3,000:1 or greater, 4,000:1 or greater, 5,000:1 or greater, 7,500:1 or greater, 10,000:1 or greater, 15,000:1 or greater. 20,000:1 or greater, 30,000:1 or greater, 40,000:1 or greater, 50,000:1 or greater, 75,000:1 or greater, or 100,000:1 or greater. The initiator may be contacted with the beta-propiolactone compound for a sufficient time to prepare polymers of the desired molecular weight. The method may comprise the step of allowing the initiator to contact the beta-propiolactone compound until a polymer composition having a number average molecular weight Mn as described herein is formed.

The beta-propiolactone compound and the initiator may be contacted at a temperature sufficient to form the polymer. The beta-propiolactone compound and the initiator may be contacted at a temperature that is sufficiently low to avoid in situ formation of undesirable unsaturated acids before or during formation of the polymer. The beta propiolactone compound and the initiator may be contacted at a temperature sufficient to initiate ring opening of the beta-propiolactone compound and form the polymer. The beta-propiolactone compound and the initiator may be maintained at a temperature of about 30° C. or greater, about 50° C. or greater, about 70° C. or greater, or about 100° C. or greater. The beta-propiolactone compound and the initiator may be maintained at a temperature of about 120° C. or less or about 100° C. or less.

The beta-propiolactone compound and the initiator may be contacted in a solvent. The solvent may be a polar aprotic solvent. The polar aprotic solvent may include amides, nitriles, sulfoxides, or any combinations thereof. The solvent may be a nonpolar solvent. The polar portic solvent may include a dialkyl ether or an alkyl cycloalkyl ether, or any combinations thereof. The beta-propiolactone compound and the initiator may be contacted in absence of a solvent. The solvent may be MTBE, THF, and/or dioxane. The method may comprise contacting the beta-propiolactone composition with a suspension of solid particles comprising the initiator, wherein the solid particles are insoluble in the beta-propiolactone compound.

The beta-propiolactone compound and the initiator may be contacted at elevated pressures. This may be done to allow processes to be conducted at temperatures above the boiling point of certain components. The beta-propiolactone compound may be contacted with the initiator at a pressure above 1 bar, about 2 bar or greater, about 3 bar or greater, about 5 bar or greater, about 10 bar or greater, about 15 bar or greater, about 20 bar or greater, about 30 bar or greater or about 40 bar or greater. The pressure may be about 50 bar or less, about 60 bar or less, about 70 bar or less, about 80 bar or less, about 90 bar or less or about 100 bar or less. The pressure may be applied by introducing a pressurized inert gas such as nitrogen or argon. the pressure may be applied by heating the mixture in a contained volume.

The beta-propiolactone compound and initiator may be contacted with a complexing agent. The addition of the complexing agent may increase the rate of the polymerization, enhancing the yield of the polymer, or may result in improved polymer properties through control of properties such as molecular weight. The complexing agent may also increase the rate of polymerization such that the polymer is formed before undesirable amounts of the beta-propiolactone compound degrade into other compounds. The complexing agent may be introduced at the beginning of the polymerization process, or at any later time. The complexing agent may be added at the same time as the initiator. The complexing agent may be added in a quantity ranging from about a 1:100 to about a 100:1 molar ratio relative to the initiator.

The beta-propiolactone compound and initiator may be contacted by a quenching agent. The quenching agent may terminate the active end of the polymer during polymerization to stop the continued growth of the polymer. The quenching agent may be added to the second chamber in an amount of less than 10 molar equivalents relative to the amount of initiator added to the chamber, for example from 0.1 to 10 molar equivalents relative to the amount of the initiator, from 0.1 to 2 molar equivalents, or from 1 to 2 molar equivalents or about 1 molar equivalent. The quenching agent may be a solid. Where the quenching agent is a solid, the polymerization mixture formed of the beta-propiolactone compound, and the initiator may flow through a fixed bed of a solid quenching agent.

The beta-propiolactone compound and initiator may also be contacted by an end capping agent. The end capping agent may quench polymerization by adding carboxylic or carboxylate functional groups to the terminal end of the formed polymer. The end capping agent may be added to the second chamber after a specified reaction time, or when the polymer has reached a desired molecular weight (e.g. when the Mn of the formed polymer exceeds a predetermined threshold). The end capping agent may be added to the second chamber in an amount of less than 10 molar equivalents relative to the amount of initiator added to the chamber, for example from 0.1 to 10 molar equivalents relative to the amount of the initiator, from 0.1 to 2 molar equivalents, or from 1 to 2 molar equivalents or about 1 molar equivalent. Examples of additional solvents, quenching agents, complexing agents, end capping agents, initiators, separation steps, equipment, and/or process conditions used in the formation of polypropiolactone may be described in WO2022221266A1, which is incorporated herein by reference in its entirety.

After contacting the beta-propiolactone compound product stream with the initiator and optionally the complexing agent, the quenching agent, or the end capping agent, the poly-3-hydroxy-propionate polymer may be formed. The polymer may then be fed to a third chamber. Alternatively, the polymer may stay in the second chamber. The second chamber and the third chamber may both be separated from the first chamber so that unwanted residues of the carbonylation catalyst may not contaminate the polymer. The polymer, an alcohol, and an esterification catalyst may be contacted in the second chamber or the third chamber.

The polymer, alcohol, and esterification catalyst may be contacted at a temperature sufficient to form an ester compound terminated by a hydroxyl group. Further, the polymer, alcohol, and esterification catalyst may be contacted at a temperature below the temperature used to produce acrylic acid. The polymer, alcohol, and esterification catalyst may be maintained at a temperature of about 70° C. or greater, about 80° C. or greater, about 90° C. or greater, about 100° C. or greater, about 110° C. or greater, about 120° C. or greater, about 130° C. or greater, about 140° C. or greater, about 150° C. or greater, or about 160° C. or greater. The polymer, alcohol, and esterification catalyst may be maintained at a temperature of about 220° C. or less, about 210° C. or less, about 200° C. or less, about 190° C. or less, or about 180° C. or less. The temperature may be maintained between about 140° C. and about 150° C. Alternatively, the temperature may be maintained about 120° C.

The exposure of a certain temperature may vary or remain constant over time so that a desired rate of formation may be achieved. For example, heat may be applied over a period of time such that a desired rate of formation of the ester compound is achieved. The rate of formation of the polymer to the ester compound may be any rate sufficient to form the ester compound. The rate of formation may change based on the temperature of the heat. Where more heat is applied, the reaction may progress to yield a greater amount of the ester compound in less time. In other embodiments, where less heat is applied, the reaction may take more time to yield the ester compound.

The polymer, alcohol, and esterification catalyst may be contacted at elevated pressures. This may be done to increase the boiling point of the alcohol so that the reaction may be performed in the liquid phase. The polymer, alcohol, and esterification catalyst may be contacted at a pressure above 1 atm or greater, about 2 atm or greater, about 3 atm or greater. The pressure may be about 7 atm or less, about 6 atm or less, or about 5 atm or less.

The polymer, alcohol, and esterification catalyst may be contacted in the absence of polymerization inhibitors. Because the polymer, alcohol, and esterification catalyst are not contacted by any polymerization inhibitors, the ester compound formed may be substantially free (Substantially free as used herein means that the reference parameter, composition, structure, or compound contains about 10 percent or less, about 5 percent or less, about 1 percent or less, about 0.5 percent or less, or about 0.1 percent or less) of any unwanted side products from the polymerization inhibitors.

The esterification catalyst may be fed to the second or third chamber in an amount sufficient to facilitate formation of the ester compound. The esterification catalyst may be added in about 0.1 weight percent or greater, about 1 weight percent or greater, about 5 weight percent or greater, about 10 weight percent or greater, or about 15 weight percent or greater. The esterification catalyst may be added in about 50 weight percent or less, about 40 weight percent or less, about 30 weight percent or less, or about 25 weight percent or less. The esterification catalyst may be added in between about 5 weight percent and about 20 weight percent.

The esterification catalyst may be separated from the ester compound after formation by any means sufficient to separate two components within a mixture, such as by extraction, distillation, precipitation by use of an additive, or any combination thereof. Alternatively, the esterification catalyst may be neutralized by adding a base to the ester compound to neutralize the esterification catalyst. The esterification catalyst may be separated from the ester compound by distillation, filtration, or oxidation, or by any suitable separation technique known in the art may be used.

The alcohol may be fed into the second or third chamber in an amount sufficient to esterify at least a portion of the polymer in the presence of the esterification catalyst. The alcohol may be added in a ratio of alcohol to polymer sufficient to achieve the desired ester compound. Further, the alcohol may be added in excess to serve as a solvent. For example, the mole ratio may be 1:1 or greater, 2:1 or greater, 5:1 or greater, 10:1 or greater, 50:1 or greater, 100:1 or greater, or 200:1 or greater. The mole ratio may be 5000:1 or less, 2500:1 or less, 1000:1 or less, or 500:1 or less.

The alcohol may be separated from the ester compound after formation. Because the alcohol may comprise excess solvent, the ester compound may utilize the removal of solvent to achieve desirable purity. The alcohol may be separated by, for example, vacuum distillation. The filtration may be used to separate the alcohol from the ester compound. Alternatively, any suitable separation technique known in the art may be used.

After formation, the ester compound may be used as a precursor in downstream applications. The formed ester compounds may be substantially free of carbonylation and/or polymerization catalysts that may have undesirable impacts in downstream formation of other products. The ester compound may be used in hard plastics. For example, the ester compound may be contacted with ammonia to form a nitrile (e.g., acrylonitrile). Techniques to form nitriles from the disclosed ester compounds may be found in at least U.S. Pat. No. 11,046,642B2, which is incorporated herein by reference it is entirety.

As used herein, the term "chamber" refers to a reactor or portion thereof where a particular reaction occurs. A "chamber" typically comprises one or more vessels with one or more connections to other reactors or system components. The methods herein place no particular limits on the type, size or geometry of the chamber employed and indeed, in some cases, more than one chamber may be employed. It is to be understood that the term "chamber" as recited in the methods herein may actually represent more than one physical chamber (for example the chamber could be a train of continuous stirred tank reactors (CSTRs) connected in parallel or in series, or a plurality of plug flow reactors). Many such combinations are known in the art and could be employed by the skilled artisan to achieve an efficient reaction in the methods described herein.

The epoxide used to prepare the beta-propiolactone compound described herein may be any epoxide that may be contacted by carbon monoxide to form the beta-propiolactone compound. The epoxide may be substituted or unsubstituted by one or more groups at one or more of the carbon atoms. The epoxide may correspond to the following formula I:

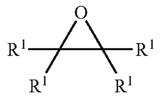

in which each $R^1$ may be independently selected from the group consisting of hydrogen; straight or branched alkyl groups; halogenated alkyl chains; phenyl groups; optionally substituted aromatic alkyl groups; aryl groups; aryl-alkyl groups; alkyl-aryl groups; optionally substituted phenyl; optionally substituted alkyl groups, or any combination thereof.

The epoxide may be one or more of: ethylene oxide, propylene oxide, butylene oxide, 4-vinylcyclohexene oxide, 4-ethylcyclohexene oxide, limonene oxide, a glycidol ether, glycidol ester or cyclohexene oxide.

The carbon monoxide may be present in any phase sufficient to form the beta-propiolactone compound. The carbon monoxide may be a pure stream or a mixture with one or more additional gases, such as hydrogen, methane, carbon dioxide, or any combination thereof.

The beta-propiolactone compound formed may have any structure sufficient to form the poly-3-hydroxy-propionate polymer described herein. The beta-propiolactone compound may be substituted or unsubstituted by one or more groups at one or more of the carbon atoms. Accordingly, the beta-propiolactone compound may correspond to the following formula II:

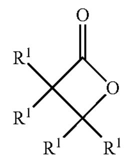

in which each $R^1$ may be independently selected from the group consisting of hydrogen; straight or branched alkyl groups; halogenated alkyl chains; phenyl groups; optionally substituted aromatic alkyl groups; aryl groups; aryl-alkyl groups; alkyl-aryl groups; optionally substituted phenyl; optionally substituted alkyl groups, or any combination thereof.

The initiator may initiate the polymerization of the beta-propiolactone compound to the poly-3-hydroxy-propionate polymer. The initiator may be any compound that ring open polymerizes the beta-propiolactone compound. The initiator may include one or more of alcohols, quaternary ammonium salts, carboxylate salts, phosphates, carboxylic acids, amines, halides, sulfonic acids, or any combination thereof. The initiator may be one or more carboxylate salts of an onium cation. The carboxylate portion may have a hydrocarbyl group bonded to the carbonyl group. The hydrocarbyl group may be an alkyl, aryl or alkyl-aryl group. The onium cation can be any onium cation which forms a salt with the carboxylate, which does not interfere with carboxylate forming an anion which can initiate anionic polymerization. For example, the initiator may be PPN-acrylate, tetramethylammonium acetate, or 1,8-diazabicyclo(5.4.0) undec-7-enium acetate.

Alternatively, the initiator may be zwitterionic, having at least one cation and at least one anion which are both covalently bound to a single molecule. The zwitterionic initiator may be an ammonium carboxylate, a phosphonium carboxylate, an ammonium sulfonate, a phosphonium sulfonate, an ammonium phosphate, or a phosphonium phosphate. For example, the zwitterionic initiator may be betaine or lauryl betaine.

The complexing agent may be any catalyst configured to increase the rate of polymerization such that the polymer is formed before undesirable amounts of the beta-propiolactone compound degrade into other compounds. Further, the complexing agent may be any compound that increases the rate of the polymerization, enhances the yield of polymer, or may result in improved polymer properties through control of properties such as molecular weight or polydispersity. The complexing agent may be a crown ether. For example, the complexing agent may be 1,4,7,10,13,16-hexaoxacyclooctadecane (18-crown-6); 1,4,7,10,13-pentaoxacyclopentadecane (15-crown-5) 1,4,7,10-tetraoxacyclododecane (12-crown-4), dibenzo 18-crown-6, 21-crown-7, or any combination thereof.

The quenching agent may be any compound which terminates the active end of the polymer during polymerization to stop the continued growth of the polymer. The quenching agent may be one or more of mineral acids, organic acids, and acidic resins or solids. The quenching agent may be HCl, H2SO4, RSO3H, HBr, H3PO4, an acidic resin, or an acidic inorganic solid. The quenching agent may be a sulfonic acid derivative, boric acid or a boric acid derivative, or phosphoric acid.

The end capping agent may be any compound that adds carboxylic or carboxylate functional groups to the terminal end of the polymer. The end capping agent may react with the terminal end groups of the polymer. The end capping agent may be any compound that sufficiently reacts with the terminal end of the polymer during polymerization of the beta-lactone compound. The end capping agent may be an electrophilic organic compound. The end capping agent may be one or more of an organohalide, organosulfonate, a haloalkyl silane, a phosphate derivative, or a boric derivative.

The polymer formed by the polymerization of the beta-propiolactone compound may be poly-3-hydroxy-propionate.

The polymer may further include the following formula IV:

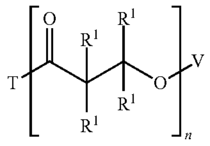

in which each $R^1$ may be independently selected from the group consisting of hydrogen; straight or branched alkyl groups; halogenated alkyl chains; phenyl groups; optionally substituted aromatic alkyl groups; aryl groups; aryl-alkyl groups; alkyl-aryl groups; optionally substituted phenyl; optionally substituted alkyl groups, or any combination thereof. The variable n is a real number greater than 1. The variable n may be chosen such that the resulting polymer may have a desired number average molecular weight. T and V are residues at the ends of the polymer.

The polymer may on one end, V, have a residue of the quenching agent. The quenching agent may inhibit the active end of the polymer from continuing to polymerize. The V may be a hydrogen.

The other end of the polymer, T, may have a residue of the initiator described herein. The polymer may have any amount of a residue of the initiator that does not prohibit use of the polymer in downstream applications, such as esterification processes. For example, the polymer may include a mass percent of a residue of the initiator of about 5 percent or less, about 3 percent or less, or about 1 percent or less, based on the total mass of the polymer. The polymer may include a mass percent of a residue of the initiator of about 0.01 percent or more, about 0.1 percent or more, or about 0.5 percent or more, based on the total mass of the polymer. For example, the polymer may have a residue of the carboxylate salt of the initiator. Alternatively, T may be a residue of the end capping agent. The end capping agent may add a carboxylic or carboxylate functional group to the terminal end of the polymer. The end capping agent may render the formed polymer more stable.

The polymer may have number average molecular weights (Mn) of greater than about 500 g/mol, 1,000 g/mol, 5,000 g/mol, 10,000 g/mol, 17,000 g/mol, 20,000 g/mol, 25,000 g/mol, 50,000 g/mol, 100,000 g/mol, 200,000 g/mol, 300,000 g/mol or 500,000 g/mol as measured as disclosed herein. The polymer may have number average molecular weights 2,000,000 g/mol or less or 1,000,000 g/mol or less. The polymer may have weight average molecular weights of greater than about 500 g/mol, 1,000 g/mol, 5,000 g/mol, 10,000 g/mol, 17,000 g/mol, 20,000 g/mol, 25,000 g/mol, 50,000 g/mol, 100,000 g/mol, 200,000 g/mol, 300,000 g/mol, 500,000 g/mol, 600,000 g/mol or 700,000 g/mol. The polymer may have number average molecular weights of 2,000,000 g/mol or less, or 1,000,000 g/mol or less. Mn of the polymer refers to that measured by gel permeation chromatography (GPC) using THE as the solvent and referenced to monodisperse polymethyl methacrylate standards.

The polymer formed herein may be substantially free of carbonylation catalyst residues. The separation of the carbonylation catalyst from the beta-propiolactone compound prior to polymerization of the compound into the poly-3-hydroxy-propionate may ensure that the polymer is substantially free of carbonylation catalyst residues. Because the polymer may be substantially free of unwanted carbonylation catalyst residues, the formed polymer may utilize little to no purification steps before use in downstream processes, such as esterification.

Further, the polymerization of the beta-propiolactone compound provides for control of the number average molecular weight of the formed polymer through the use of the initiator and the quenching agent. The formation of the polymer by the polymerization of the beta-propiolactone compound also provides for control of the end groups of the formed polymer. The end groups of the formed polymer, which may or may not be residues of the initiator, may be present in amounts that do not prohibit use of the polymer in downstream processes. The end groups may be selected to stabilize the formed polymer. Alternatively, the end groups may be selected to improve reaction conditions of the polymer in downstream process. Therefore, the polymer formed herein may have favorable weights, selective end groups, and little to no unwanted residues, thereby utilizing less steps and enhancing efficiency in the application of the polymer downstream.

The alcohol present in the esterification step may be any alcohol that, when contacted with the polymer in the presence of an esterification catalyst, may form an ester. The alcohol may be a straight chain alcohol. Alternatively, the alcohol may be a branched chain alcohol. The alcohol may be cyclic. The alcohol may be substituted. In other embodiments, the alcohol may be unsubstituted. The alcohol may have an alkyl group. In certain embodiments, the alcohol may have an aryl group. In other embodiments, the alcohol may have an alkyl-aryl or an aryl-alkyl group. The alcohol may have a $C_1$-$C_{20}$ alkyl group. For example, the alcohol may have one or more methyl, ethyl, propyl, or butyl groups, or any combination thereof. Alternatively, the alcohol may have one or more isopropyl, isobutyl, tert-butyl, or sec-butyl groups, or any combination thereof. In other embodiments, the alcohol may have one or more phenyl, tolyl, xylyl, or naphthyl groups, or any combination thereof. The alcohol may be any alcohol known in the art to esterify a polymer. For example, the alcohol may be methanol, ethanol, propanol, or butanol. Alternatively, the alcohol may be isopropanol, isobutanol, tert-butanol, or sec-butanol.

The esterification catalyst may be any catalyst that, when contacted by a polymer and an alcohol, may improve the esterification of the polymer by the alcohol. The esterification catalyst may improve the reaction conditions of the esterification of the polymer. The esterification catalyst may increase a rate of formation of the ester compound. The rate of formation of the ester compound may be any sufficient rate of production of the ester compound. The esterification catalyst may facilitate the formation of the ester compound. The esterification catalyst may be an acid catalyst. For example, the catalyst may be phosphoric acid. Alternatively, the esterification catalyst may be a sulfur catalyst. For example, the esterification catalyst may be sulfuric acid, p-toluenesulfonic acid, or camphorsulfonic acid. The esterification catalyst may be in a solid phase. For example, the esterification catalyst may be Amberlite IR200 hydrogen form. In other embodiments, the esterification catalyst may be in a liquid phase. The esterification catalyst may be a phosphate. For example, the esterification catalyst may be diphenyl phosphate.

The ester compound may have a hydroxyl group connected to an alkyl chain of at least three carbons. The alkyl chain may be substituted or unsubstituted. The ester compound may have a residue of the alcohol. The ester compound may be substantially free of unwanted residues. Because of the separation of carbonylation catalyst from the beta-propiolactone compound and the use of two or more separate chambers, the ester compound may be free of carbonylation catalyst residues, thereby eliminating the need for purification of the ester compound, reducing the number of steps in the production of the ester compound.

The ester compound may be formed by the methods disclosed herein. The ester compound may have the following formula III:

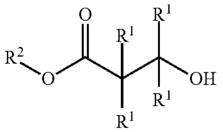

in which each $R^1$ may be independently selected from the group consisting of hydrogen; straight or branched alkyl groups; halogenated alkyl chains; phenyl groups; optionally substituted aromatic alkyl groups; aryl groups; aryl-alkyl groups; alkyl-aryl groups; optionally substituted phenyl; optionally substituted alkyl groups, or any combination thereof, and in which $R^2$ may be a residue of the alcohol having one of a straight or branched alkyl group; aryl group; alkyl-aryl group; or aryl-alkyl group.

A composition including the ester compound may have any one of the following formulas:

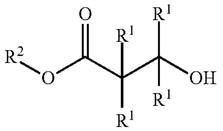

-continued

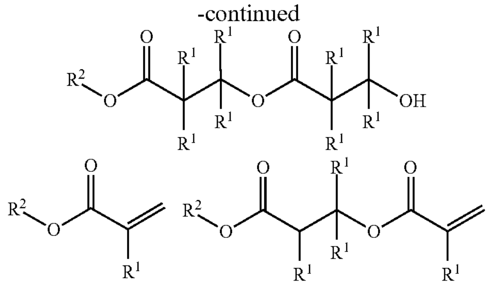

in which each $R^1$ may be independently selected from the group consisting of hydrogen; straight or branched alkyl groups; halogenated alkyl chains; phenyl groups; optionally substituted aromatic alkyl groups; aryl groups; aryl-alkyl groups; alkyl-aryl groups; optionally substituted phenyl; optionally substituted alkyl groups, or any combination thereof, and in which each $R^2$ may be a residue of the alcohol having one of a straight or branched alkyl group; aryl group; alkyl-aryl group; or aryl-alkyl group.

The composition may include a residue of a poly-3-hydroxy-propionate, a residue of a poly-3-hydroxy-propionate initiator, and a residue of an esterification catalyst. The residue of the poly-3-hydroxy-propionate may form the backbone of the ester compounds found in the composition. The ester compounds that may be found in the composition may have residues of the poly-3-hydroxy-propionate initiator. The residues of the initiator may be present in amounts that do not prohibit the use of the ester compounds in downstream applications. For example, the residue of the initiator may be present in a mass percent of about 5 percent or less, about 3 percent or less, or about 1 percent or less, based on the total mass of the esterified poly-3-hydroxy-propionate polymer. The residue of the initiator may be present in a mass percent about 0.01 percent or more, about 0.1 percent or more, or about 0.5 percent or more, based on the total mass of the esterified poly-3-hydroxy-propionate polymer. The ester compounds of the composition may also include residues of the esterification catalyst. The residues of the esterification catalyst may be present in amounts that do not prohibit the use of the ester compounds in downstream applications. For example, the esterification catalyst may be present in residues of 0.1 weight percent or greater, about 1 weight percent or greater, about 5 weight percent or greater, about 10 weight percent or greater, or about 15 weight percent or greater. The esterification catalyst may be present in residues of about 50 weight percent or less, about 40 weight percent or less, about 30 weight percent or less, or about 25 weight percent or less.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

EXAMPLES

Example 1

The below reaction contacts poly(3-hydroxy propanoate) ("P3HP"), 1-butanol, and an acid catalyst according examples 1-6. The reactions are carried out with 0.5 g of P3HP powder with 2% (by mass) acid catalyst in 5 mL of 1-butanol. The mixtures are heated to 100° C. for 4 hours. Products were analyzed by a gas chromatographer Agilent Technologies GC-TCD. Results are shown Table 1 and illustrate which of the products were formed and the amount of polymer converted.

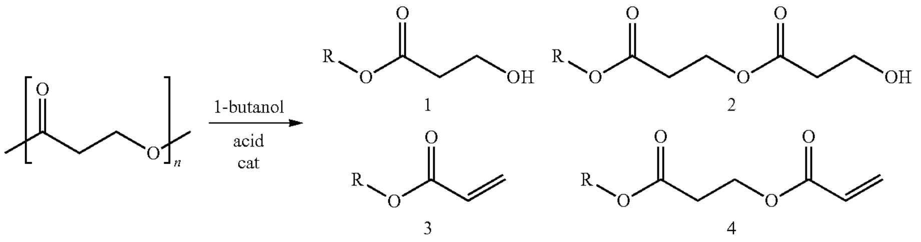

| Example # | catalyst | Conversion % | % 1 | % 2 | % 3 | % 4 |
|---|---|---|---|---|---|---|
| 1 | Sulfuric acid | quant | 85 | 14 | <1 | <1 |
| 2 | Phosphoric acid | 5 | 5 | 92 | 3 | 0 |
| 3 | p-Toluenesulfonic acid | 53 | 69 | 29 | 1 | 1 |
| 4 | Camphorsulfonic acid | 13 | 2 | 95 | 2 | 1 |
| 5 | Amberlite IR200 hydrogen form | 2 | 15 | 66 | 13 | 6 |
| 6 | Diphenyl phosphate | 1 | 37 | 27 | 18 | 18 |

Example 2

FIG. 1 illustrates a reaction scheme of contacting a polypropiolactone polymer, ethanol, and a catalyst to form a an ester compound and associated NMR data of ester compounds formed from the disclosed scheme. 2 mol % $H_2SO_4$ in 40 mL of ethanol is added to 4 g of P3HP pellets. The NMR is a Bruker Avance 400 MHz. The reaction is refluxed for 24 h. Before the ethanol is removed by vacuum, the product is extracted in $CHCl_3$ and washed with sodium bicarbonate solution. The product is dried by vacuum to give 3.32 g of product (51% yield) The NMR indicated that the final product contained unreacted P3HP (8%) (4.38 and 2.65 ppm). The NMR spectrum does not show evidence of hydroxy ester dimer (compound 2, table 1) or ethyl acrylate.

Example 3

Figure 2:
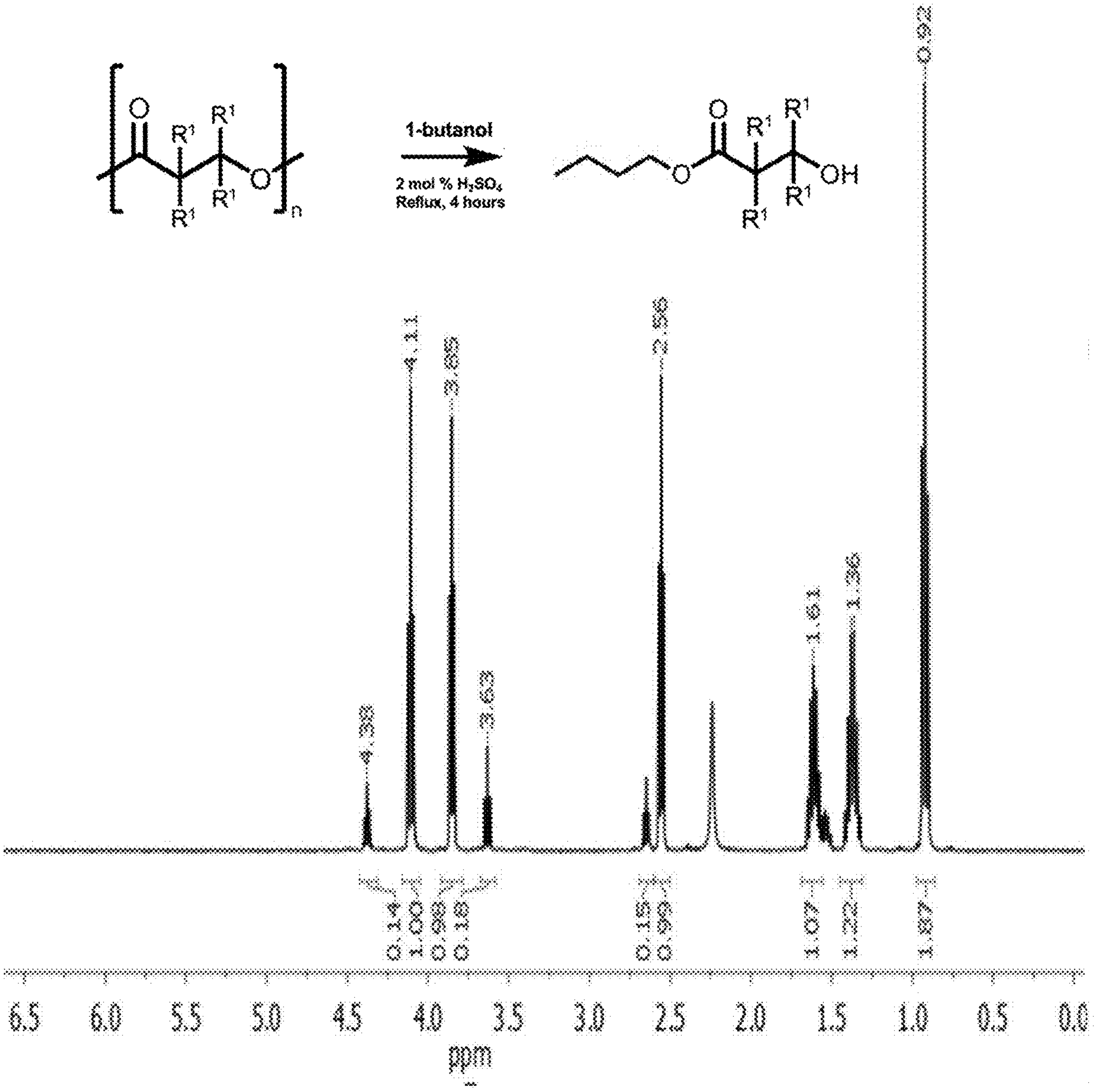
FIG. 2 is illustrates a reaction scheme of contacting a polypropiolactone polymer, ethanol, and a catalyst to form a an ester compound and associated NMR data of ester compounds formed from the disclosed scheme.

FIG. 2 is illustrates a reaction scheme of contacting a polypropiolactone polymer, ethanol, and a catalyst to form a an ester compound and associated NMR data of ester compounds formed from the disclosed scheme. 2 mol % $H_2SO_4$ in 40 mL of 1-butanol is added to 4 g of P3HP pellets. The NMR is the same as Example 2. The reaction is refluxed for 4 h. Before the butanol is removed by vacuum, the product is extracted in $CHCl_3$ and washed with sodium bicarbonate solution. The product is dried by vacuum to give 6.67 g of product (83% yield). Product contained unreacted P3HP (14%) (4.38 ppm) and 1-butanol (3.63 ppm) indicated by the NMR spectrum. The NMR spectrum does not show evidence of hydroxy ester dimer (compound 2, table 1) or butyl acrylate.

What is claimed is:

1. A method comprising:

contacting an epoxide and carbon monoxide to form a beta-propiolactone compound;

contacting the beta-propiolactone compound and an initiator to form poly-3-hydroxy-propionate; and contacting the poly-3-hydroxy-propionate, an alcohol, and an esterification catalyst at a temperature sufficient to form an ester compound terminated by a hydroxyl group.

2. The method of claim 1, wherein the epoxide and the carbon monoxide are contacted in a first chamber.

3. The method of claim 2, wherein the beta-propiolactone compound and the initiator are contacted in a second chamber that is separated from the first chamber.

4. The method of claim 3, wherein the poly-3-hydroxy-propionate, the alcohol, and the esterification catalyst are contacted in the second chamber or a third chamber that are each separated from the first chamber.

5. The method of claim 1, wherein the epoxide and the carbon monoxide are contacted in presence of a carbonylation catalyst.

6. The method of claim 5, further comprising:

separating the beta-propiolactone compound from the carbonylation catalyst so that the beta-propiolactone compound is free of residues of the carbonylation catalyst.

7. The method of claim 1, wherein the epoxide comprises a formula:

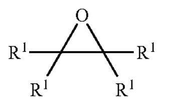

wherein each $R^1$ independently comprises one or more of hydrogen, straight or branched alkyl groups, aryl groups, alkyl-aryl groups, aryl-alkyl groups, or any combination thereof.

8. The method of claim 1, wherein the beta-propiolactone compound comprises a formula:

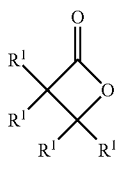

wherein each $R^1$ independently comprises one or more of hydrogen, straight or branched alkyl groups, aryl groups, alkyl-aryl groups, aryl-alkyl groups, or any combination thereof.

9. The method of claim 1, further comprising:

separating the ester compound from the alcohol and/or the esterification catalyst.

10. The method of claim 9, wherein the separation of the ester compound may be performed by distillation, filtration, or oxidation.

11. The method of claim 1, wherein the ester compound comprises a hydroxyl group connected to an alkyl chain of at least three carbons.

12. The method of claim 1, wherein the ester compound comprises a formula:

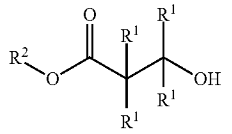

wherein each $R^1$ independently comprises one or more of hydrogen, straight or branched alkyl groups, aryl groups, alkyl-aryl groups, aryl-alkyl groups, or any combination thereof, and wherein $R^2$ comprises a straight or branched alkyl group, aryl group, alkyl-aryl group, or aryl-alkyl group.

13. The method of claim 5, wherein the ester compound is free of residues of the carbonylation catalyst.

14. The method of claim 1, wherein the esterification catalyst is configured to facilitate formation of the ester compound.

15. The method of claim 1, wherein the esterification catalyst comprises an acid catalyst.

16. The method of claim 1, wherein the alcohol comprises one or more straight or branched alkyl, aryl, alkyl-aryl, or aryl-alkyl groups.

17. The method of claim 1, wherein the contacting of the poly-3-hydroxy-propionate by the alcohol and the esterification catalyst is free of polymerization inhibitors.

18. The method of claim 1, wherein the ester compound is contacted with an amide to form an acrylonitrile compound.

19. A composition comprising:

an ester compound that is a residue of a poly-3-hydroxy-propionate, a residue of a poly-3-hydroxy-propionate initiator, and a residue of an esterification catalyst.

20. The composition of claim 19, wherein the ester compound comprises any one formula:

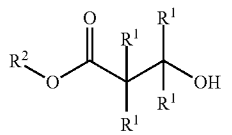

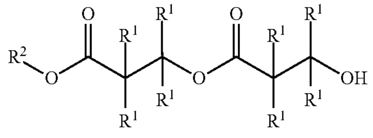

-continued
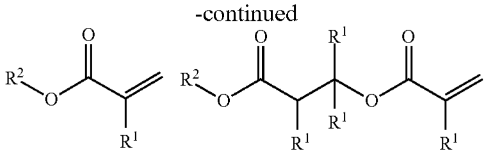
wherein each $R^1$ independently comprises one or more of hydrogen, straight or branched alkyl groups, aryl groups, alkyl-aryl groups, aryl-alkyl groups, or any combination thereof, and wherein $R^2$ comprises a straight or branched alkyl group, aryl group, alkyl-aryl group, or aryl-alkyl group.
* * * * *